(12) United States Patent
Schoenmaekers et al.

(10) Patent No.: US 8,199,878 B2
(45) Date of Patent: Jun. 12, 2012

(54) METHODS AND SYSTEMS FOR PERFORMING DIFFERENTIAL RADIOGRAPHY

(75) Inventors: Walter Schoenmaekers, Tielt-winge (BE); Luc Van Hoorebeke, Ghent (BE); Bert Masschaele, Kemmel (BE); Veerle Cnudde, Nukerke (BE); Manuel Dierick, Nazareth (BE); Jelle Vlassenbroek, Nieuwerkerken (BE)

(73) Assignee: Sutor BVBA, Tielt-Winge (BE)

( * ) Notice: Subject to any disclaimer, the term of this patent is extended or adjusted under 35 U.S.C. 154(b) by 232 days.

(21) Appl. No.: 12/595,769
(22) PCT Filed: Apr. 10, 2008
(86) PCT No.: PCT/EP2008/054368
§ 371 (c)(1), (2), (4) Date: Oct. 13, 2009
(87) PCT Pub. No.: WO2008/125596
PCT Pub. Date: Oct. 23, 2008

(65) Prior Publication Data
US 2010/0060633 A1  Mar. 11, 2010

(30) Foreign Application Priority Data
Apr. 13, 2007 (EP) .................................. 07447026

(51) Int. Cl.
*H05G 1/64* (2006.01)
(52) U.S. Cl. ..................... 378/98.11; 378/57
(58) Field of Classification Search ............ 378/62, 378/57, 98.11, 98.12
See application file for complete search history.

(56) References Cited

U.S. PATENT DOCUMENTS
2006/0062446 A1  3/2006  Porat

OTHER PUBLICATIONS

Baechler, Materna, Jolie, Cauwels, Gritting, Honkimaki, Johner, Masschaele, Mondelaers, Kern, Piboule: "Non-destructive analysis of a bulky sample from a natural fossil reactor", Journal of Radioanalytical and Nuclear Chemistry, vol. 250, No. 1, Jul. 19, 2000, pp. 39-45, XP002447823.

B. Masschaele, M. Dierick, L. Van Hoorebeke, V. Cnudde, P. Jacobs: "The use of neutrons and monochromatic x-rays for non-destructive testing in geological materials", Environmental Geology, vol. 46, Jul. 20, 2003, pp. 386-492, XP002447824.

B. Masschaele, S. Baechler, P. Cauwels, J. Jolie, W. Mondelaers, M. Dierick: "Cold neutron and monochromatic x-ray micro-tomogrphy", AIP, $16^{16}$ International Conference, Application of Accelerators in Research and Industry, 2001, pp. 1095-1098, XP002447825.

*Primary Examiner* — Courtney Thomas
(74) *Attorney, Agent, or Firm* — Bacon & Thomas, PLLC

(57) ABSTRACT

The present invention relates to a characterization system (100) for characterizing an object (104) comprising a basic material and additional structural features. The system (100) comprises at least one irradiation source (102) for generating an irradiation beam for irradiating the object (104) to be characterized and at least one detector (106) for detecting said irradiation beam transmitted through the object (104). The system (100) furthermore comprises a control means (108) for obtaining at least two different basic datasets of the object (104) for different configurations of the irradiation beam, the object (104) and the detector (106). The latter may be obtained by shifting and/or rotating components and/or by selecting different components used for acquisition of the datasets. The system furthermore comprises an image processing means (112) for combining said at least two different basic datasets as to obtain a differential image indicating the additional structural features of the object (104) but substantially filtering out the basic material. The invention also relates to a corresponding method for characterizing objects and to an image processing means for processing acquired images accordingly.

20 Claims, 11 Drawing Sheets

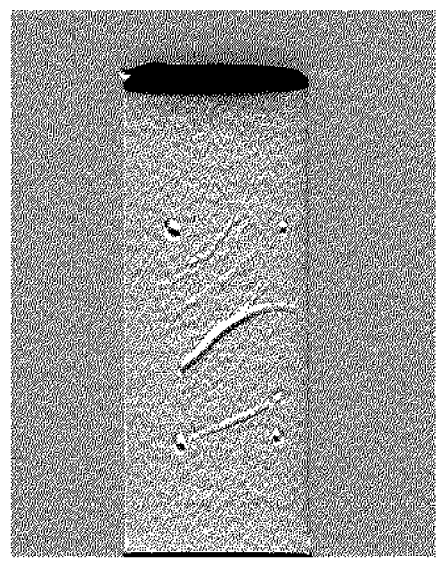
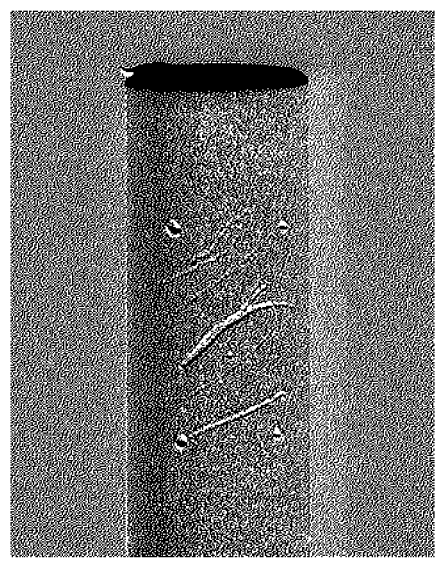
Fig. 15b      Fig. 15c
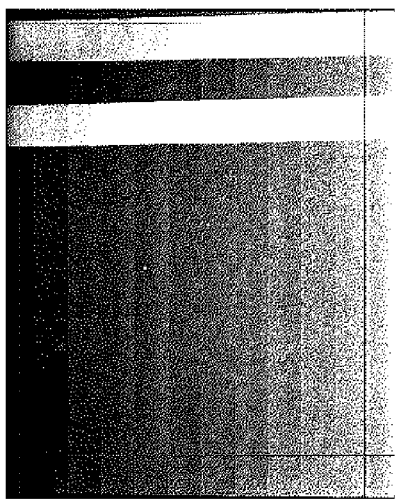
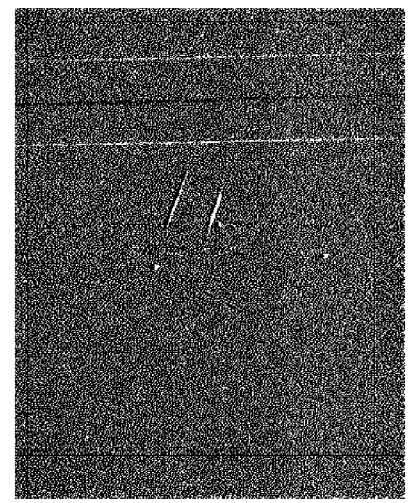
Fig. 16a      Fig. 16b
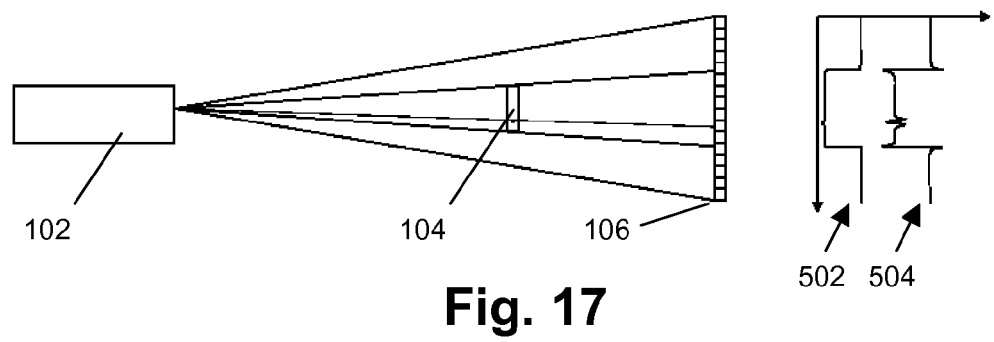
Fig. 17

METHODS AND SYSTEMS FOR PERFORMING DIFFERENTIAL RADIOGRAPHY

TECHNICAL FIELD OF THE INVENTION

The present invention relates to the field of material characterisation. More particularly, the present invention relates to methods and systems for characterising or inspecting materials such as but not limited to raw or polished gemstone or diamonds.

BACKGROUND OF THE INVENTION

Material inspection and material characterisation can be done using a number of existing techniques. Some examples are radiography, digital radiography, microscopy, computed tomography, etc. These techniques are imaging techniques allowing visualisation of objects and features thereof. One example of current material characterisation is the inspection of diamonds using visible light. As such visible inspection often suffers from internal reflections in the diamond, it is often difficult to determine the exact location of defects or faults in the stone. Nevertheless, appropriate localisation of defects is required in order to correctly process the diamond.

One known characterisation technique for the study of gemstone is described in US2006/0062446. The document describes the use of different X-ray images of an object for characterising contour lines of the object or features therein. The X-ray images are made by providing a relative rotation of the object with respect to the source and the detector. The X-ray images thereby are taken from substantially different angles. In order to obtain a three dimensional image, the X-ray images are introduced in a three-dimensional model of the gemstone's outer contours. Although some other techniques also are available, there is a need for a fast imaging technique allowing to localise features in an object with good resolution and contrast.

SUMMARY OF THE INVENTION

It is an object of the present invention to provide good apparatus or methods for characterising objects. More particularly, it is an advantage of embodiments of the present invention that good apparatus or methods are provided for visualising structural features present in objects. Such structural features may be structural defects or foreign materials being present. It is an advantage of embodiments of the present invention that 2D digital images of objects can be obtained allowing identification of internal features and contour features of the object. It is an advantage of embodiments of the present invention that 3D digital images of objects can be obtained allowing identification of internal features and contour features of the object. It is an advantage of embodiments according to the present invention that, by using differential imaging, e.g. differential radiography, a distinction between the bulk information and the defects can be made. Differential imaging, e.g. differential radiography, thereby refers to an imaging technique whereby through combination of images sub-images, e.g. division or subtraction of sub-images, an image of interest is obtained. It is furthermore an advantage of some embodiments of the present invention that the defects can be localized inside the 3D volume of the object. It is an advantage of embodiments of the present invention, that the methods and systems are especially suitable for characterising diamonds. It is furthermore an advantage that methods and system can be easily combined with other automatic inspection techniques and that in this way an automatic characterisation technique can be obtained providing info on the clarity of objects, e.g. of diamonds. It is an advantage of embodiments of the present invention that a fast characterisation technique is obtained. It is an advantage of embodiments according to the present invention that by experimentally determining differential images, the detector response can be appropriately filtered out, resulting in a good signal to noise ratio. It is an advantage of embodiments according to the present invention that determination of the three dimensional position of features in the objects can be determined.

It is an advantage of embodiments according to the present invention that three dimensional position information of features in the objects can be obtained using only a single differential image. A good signal to noise ratio thereby can be determined. It is an advantage of embodiments according to the present invention that artefacts due to detector response, X-ray scattering, X-ray beam hardening and beam inhomogeneity can be at least partly compensated for.

The above objective is accomplished by a method and device according to the present invention.

The present invention relates to a characterisation system for characterising an object comprising a basic material and additional structural features, the system comprising at least one irradiation source for generating an irradiation beam for irradiating the object to be characterised and at least one detector for detecting said irradiation beam transmitted through the object, the system furthermore comprising a control means adapted for controlling said characterisation system to obtain at least two different basic data sets, i.e. images, of the object for different configurations of the irradiation beam, the object and the detector, and an image processing means adapted for combining said at least two different basic data sets, i.e. images, and adapted for obtaining based thereon a differential image, e.g. an at least one dimensional differential image or e.g. an at least two dimensional differential image, indicating the additional structural features of the object but substantially filtering out the basic material so that the basic material is not indicated in the differential image. The different configurations may be different geometric configurations.

It is an advantage of embodiments of the present invention that only a small number of images is required for obtaining the differential image, resulting in a time and cost efficient system.

The image processing means may be adapted for any or a combination of dividing and/or subtracting the at least two different basic dataset, i.e. images. It is an advantage of embodiments according to the present invention that the number of different calculations required for obtaining appropriate two-dimensional positional information on the structural features is limited compared to conventional computed tomography methods, resulting in a computational efficient system. It is an advantage of embodiments of the present invention that the structural features are visualised with a high contrast.

The at least two different basic datasets, e.g. images, may be two different basic data sets, e.g. images. It is an advantage of embodiments according to the present invention that only two basic data sets, e.g. images, need to be acquired to obtain useful information concerning the 2-dimensional position of additional structural features in the object, resulting in a time efficient system. The at least one irradiation source may be adapted for providing a flood irradiation of the object. The flood irradiation may be irradiation such that the whole object or part of interest of the object is irradiated at once. It is an advantage of embodiments of the present invention that a time efficient system is obtained.

The basic material may be substantially uniform and the additional structural features may be features of interest. Such features of interest may for example be wanted defects and/or unwanted defects.

The control means may be adapted for providing different configurations of the irradiation beam, the object and the detector by providing a relative shift between any of the irradiation beam, the object and the detector. It is an advantage of embodiments of the present invention that the basic dataset, i.e. images required can be acquired in an easy way.

The detector may have detector pixels of a predetermined size P and the relative shift may result in a shift between the basic datasets, e.g. images, of more than the predetermined pixel size P but less than 100% of the field of view of the imaging system, preferably less than 10% of the field of view of the imaging system, more preferably less than 1% of the field of view of the imaging system. It is an advantage of embodiments according to the present invention that corresponding defects in the different basic dataset, i.e. images can be easily correlated and that these are imaged with a high contrast. The shift between the basic datasets, e.g. images, may be smaller than the predetermined pixel size P, e.g. down to 0.1 times the predetermined pixel size, or down to 0.5 times the predetermined pixel size.

The control means may be adapted for providing at least a shift in the direction perpendicular to an irradiation source-detector axis. Such a shift may results in a difference in magnification for the basic images or corresponding datasets. The control means may be adapted for providing at least a shift in the direction parallel to an irradiation source-detector axis. Such a shift may results in an overall shift between the basic images or corresponding datasets.

The characterisation system may comprise at least two irradiation sources and/or at least two detectors, wherein the control means may be adapted for providing said shift by selecting a different irradiation source and/or selecting a different detector for acquiring a second of the at least two basic datasets, i.e. images.

The control means may be adapted for providing different configurations of the irradiation beam, the object and the detector by providing a relative rotation between any of the irradiation beam, the object and the detector.

The control means may be adapted for providing a relative rotation of less than 5°, preferably less than 3°, more preferably less than 1°.

The control means may be adapted for providing a relative rotation of the object of substantially 180° and the image processing means is adapted for, prior to said combining, mirroring one of the at least two basic datasets, i.e. images.

The irradiation source may be adapted for generating a non-parallel irradiation beam. The irradiation beam may be a non-parallel beam, i.e. a diverging or converging beam. The irradiation beam may be a conical beam.

The image processing means may furthermore be adapted for deriving three-dimensional positional information based on said differential image. It is an advantage of embodiments of the present invention that, based on the at least two basic datasets, i.e. images, e.g. two basic datasets, i.e. images, three dimensional location of defects in an object can be performed. The three-dimensional positional information may be derived taking into account a shift of imaged internal features between the at least two different basic datasets, i.e. images.

The image processing means may be adapted for deriving three dimensional position information based on a combination of a plurality of differential images.

The different configuration may be obtained by a translation of the object on a translation means. The translation means may be a conveyor belt.

The at least one irradiation source may be an X-ray irradiation source and the at least one detector may be a two dimensional X-ray detector.

The image processing means may be adapted for generating a three dimensional image of the additional features.

The system may be adapted for extracting phase contrast information of the additional features.

The present invention also relates to a method for characterising an object comprising a basic material and additional structural features, the method comprising obtaining at least two different basic datasets, i.e. images, of the object for different positional configurations of the object and the at least one irradiation source and the at least one detector used for imaging the object, combining the at least two different basic datasets, i.e. images, and obtaining based thereon a differential image indicating the additional structural features of the object but substantially filtering out the basic material. The differential image may be an at least one dimensional differential image. The differential image may for example also be an at least two dimensional differential image. Obtaining the at least two different basic datasets, i.e. images, may comprise acquiring a first basic dataset, i.e. image, for a first positional configuration of the object, the at least one irradiation source and the at least one detector, providing a second, different positional configuration of the object, the at least one irradiation source and the at least one detector, and acquiring a second basic dataset, i.e. image, for the second positional configuration of the object, the at least one irradiation source and the at least one detector.

The method furthermore may comprise deriving three dimensional positional information for the additional structural features based on said differential image.

The method furthermore may comprise extracting phase contrast information of the additional structural features of the object.

The present invention furthermore relates to an image processing means for use in characterisation of objects comprising a basic material and additional structural features, the image processing means being adapted for receiving a first basic dataset, i.e. image, acquired for a first positional configuration and for receiving a second basic dataset, i.e. image, acquired for a second positional configuration, different from the first positional configuration, and combining the at least two different basic datasets, i.e. images, so as to obtain a differential image, e.g. an at least one-dimensional differential image or e.g. an at least two-dimensional differential image, indicating the additional structural features of the object but substantially filtering out the basic material. The image processing means furthermore may be adapted for determining three dimensional positional information of the additional structural features of the object based on the differential image.

For determining three dimensional positional information, the image processing means may take into account information about configurations used for acquiring the images received.

The image processing means may be adapted for extracting phase contrast information of the object.

The present invention also relates to a computer program product adapted for, when executed on a computing device, performing a method for obtaining an image of one or more volumetric sections of a sample as set out above. The invention furthermore relates to a machine readable data storage device storing such a computer program product and/or the transmission of the computer program product over a local or wide area telecommunications network.

The present invention also relates to digital or analogue images produced by any of the methods as described above.

In one aspect, the present invention also relates to a characterisation system for characterising or imaging an object, the system comprising at least one irradiation source for generating an irradiation beam for irradiating the object to be characterised or imaged and at least one detector for detecting said irradiation beam transmitted through the object, the system furthermore being adapted for extracting phase contrast information of the object, e.g. generating an phase contrast image of the object, based on a differential image. It also relates to a method for characterising an object comprising a basic material and additional structural features, the method comprising obtaining at least one basic dataset, i.e. image, of the object comprising phase contrast information for the object. The invention also relates to a corresponding image processor for processing phase contrast information and to corresponding computer program products.

It is an advantage of embodiments according to the present invention using differential imaging that artifacts caused by the imaging set-up may be automatically removed from the image of interest.

Particular and preferred aspects of the invention are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIG. 13a to FIG. 16b illustrate different differential images and comparison with standard X-ray images illustrating advantages of embodiments according to the present invention.

FIG. 17 illustrates exploitation of phase contrast enhancement for characterising objects, according to embodiments of the present invention.

Figure 1:
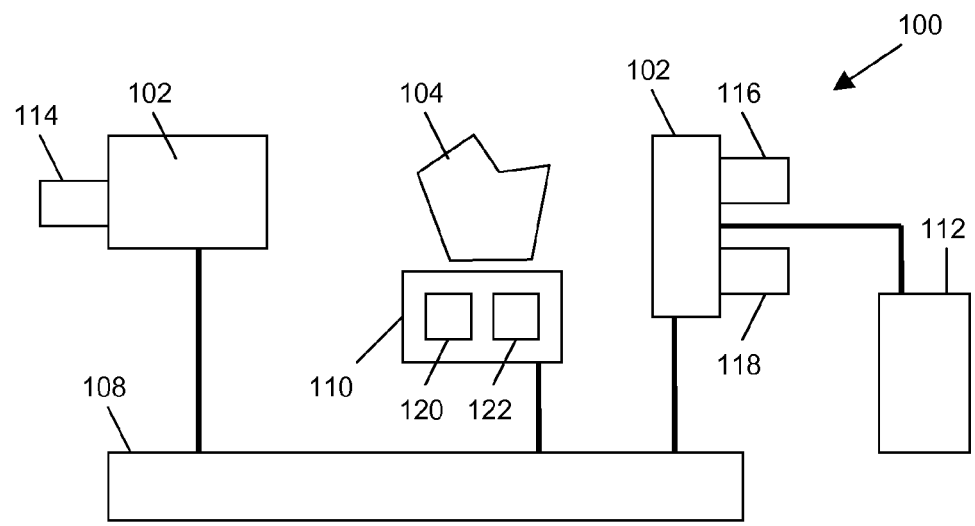
FIG. 1 is a schematic representation of a characterisation system according to embodiments of the first aspect of the present invention.

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first and second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B. Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms are provided solely to aid in the understanding of the invention.

Differential imaging, e.g. differential radiography, thereby refers to an imaging technique whereby through combination of datasets, i.e. images or sub-images, e.g. any or a combination of a division and/or subtraction of datasets, an image of interest is obtained. A differential image thereby may refer to a single image which is the result of a combination of two or more datasets acquired as images using a different relative source, object and detector geometry. The combination may be a calculation such as for example any or a combination of divisions and/or subtractions. A differential image allows to remove the effect of the detector response and the bulk material of the studied object. The differential image may be at least a one dimensional image. The differential image also may for example be at least a two dimensional image. The terms "irradiating", "radiation" refer to electromagnetic radiation which may be any type of electromagnetic radiation such as e.g. infrared radiation, visible light, UV radiation, X-ray radiation, . . . . X-ray radiation thereby may be ionising electromagnetic radiation produced by charged particles, such as e.g. electrons is meant, with an energy above 0.1 keV, up to several MeV. In particular embodiments, the energy of the X-rays may be between 0.1 keV and 1000 keV, e.g. between 0.1 keV and 100 keV. In practice, the lower limit may be determined by the energy of the X-rays required to penetrate the bulk of the sample. In the present example the electromagnetic radiation preferably is penetrating radiation, i.e. the irradiation beam is substantially transmitted through the object.

The object may be a solid object or a fluid object. It comprises a basic material and additional structural features. The basic material may be for example a matrix, a raster, a bulk, etc. The objects preferably have a uniform base material, e.g. matrix, or a non-uniform matrix without large discontinuities. Large discontinuities thereby may be discontinuities whereby the mass absorption coefficient varies more than 100% or more than 50% within 10% of the field of view of the imaging system.

The systems and methods of the present invention are especially suitable for base materials with a uniform bulk or quasi-repetitive bulk. The based material thereby may be the uniform bulk of the object without unwanted artefacts. Additional structural features, which also may be referred to as defects, may comprise internal features and external features. The additional features may be features of interest, such as for example wanted defects and/or unwanted defects. The internal features may be for example holes or inclusions, raster defects, absorbing defects, crystallographic defects, although the invention is not limited thereto. External features, which may also be referred to as contour features, may be for example scratches or edges of the material, coatings, although the invention is not limited thereto. The object may e.g. be a raw or polished gemstone or diamond, but the invention is not limited thereto and also may be for example crystals, stones, liquids, a consumer product such as food products or beverages, ceramics, metals, tissues or more in general a material to be characterised. The internal features or external features may have a typical dimension of less than 10%, preferably less than 5%, more preferably less than 3% of the largest dimension of the field of view.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims. In a first aspect, the present invention relates to a characterisation system for characterising objects, more particularly for visualizing internal features and contour features of an object. By way of example, a schematic overview of different basic and optional components are illustrated in FIG. 1. The characterisation system 100 comprises a at least one irradiation source 102 adapted for generating an irradiation beam for irradiating the object 104. The irradiation source 102 preferably is selected such that the irradiation beam is penetrating for the object 104, i.e. the irradiation beam is transmitted through the object 104. The characterisation system 100 furthermore comprises at least one detector 106 adapted for detecting the irradiation beam after it has been transmitted through the object. The at least one detector 106 may therefore allow to obtain a basic dataset, i.e. image, of the object 104. The characterisation system 100 furthermore comprises a control means 108, e.g. a controller, for controlling the characterisation system for obtaining at least two different basic datasets, i.e. images, of the object 104 for different configurations of the irradiation beam, the object 104 and the at least one detector 106. The basic datasets thereby may be conventional X-ray absorption images of the object. The control means 108 therefore may be connected to and controlling the irradiation source 102, to a positioning means 110 for positioning the object 104 such as e.g. a sample stage and/or the detector 106. The characterisation system 100 also comprises an image processing means 112, e.g. an image processor, adapted, e.g. programmed, for combining the at least two different basic datasets, i.e. images, and adapted to obtain, based on said combined at least two different basic datasets, a differential image indicating the additional structural features of the object 104 but substantially filtering out the imaged basic material. The obtained differential image may be an at least one dimensional differential image. The differential image may also be an at least two dimensional differential image.

The different components of the characterisation system 100 will, by way of example, further be described in more detail, indicating optional features of these components.

The system 100 typically comprises an irradiation source 102 which may be an electromagnetic radiation source for providing an electromagnetic irradiation beam. The irradiation beam may have any type of beam shape. In some preferred embodiments, the irradiation beam may have a non-parallel irradiation beam, e.g. a conical beam shape. The irradiation beam may for example originate from a point irradiation source or point-like irradiation source, i.e. having a small emission surface compared to the object and detector. In preferred embodiments, the irradiation source is adapted for generating an irradiation beam which is largely divergent, e.g. with a large cone beam opening, as the latter may assist in ease for determining three dimensional location information about objects. It is an advantage of the use of such irradiation beams that information about the position in a direction along the source 102-detector 106 axis can be obtained from the basic datasets, i.e. images, recorded. In other preferred embodiments, the irradiation beam may have a parallel beam shape. The irradiation beam may be a polychromatic beam. The irradiation beam preferably comprises wavelengths such that the irradiation beam is penetrating for the object, i.e. that the irradiation beam is substantially transmitted through the object 104. In other words, the irradiation source 102 may be an irradiation source allowing to obtain an image, e.g. transmission image of the sample. The irradiation source may for example be an infrared irradiation source, a visible irradiation source, an ultraviolet irradiation source or an X-ray irradiation source. In a large number of applications, the irradiation source preferably is an X-ray irradiation source such as e.g. an X-ray radiation tube of well known conventional design, or a field emission X-ray radiation source. The irradiation source 102 also may be provided with a cooling means 114 allowing cooling of the irradiation source 102. Typically such an irradiation source 102 may be water-cooled. The irradiation source 102 preferably is adapted for providing flood lighting of the object, i.e. such that the whole object or the whole part of interest of the object is irradiated at once. The irradiation source 102 may be positioned on a moveable stage in order to provide a different configuration between the detector 106 and the source 102 and/or object 104. Alternatively or in addition thereto, the irradiation source 102 may be adjustable so as to adjust the beam shape or beam position in order to provide a different configuration between the detector 106 the irradiation beam from the irradiation source 102 and the object 104. The at least one irradiation source 102 also may be a plurality of irradiation sources, such as e.g. two irradiation sources 102, whereby different irradiation sources are used for the recording of two basic datasets, i.e. images, for different configurations between the irradiation beam of the irradiation source 102 used, the object 104 and the detector 106.

The at least one detector 106 may be any suitable imaging detector for detecting the transmitted irradiation beam, transmitted through the object. The detector 106 may be a pixelated detector. The detector 106 may be a digital area detector. The detector 106 may be a two-dimensional pixelated detector for imaging the whole image at once or a one dimensional pixelated detector allowing to detect a line or a single detector element or group of single detector elements. In the case of a one dimensional pixelated detector or if a single detector element would be used, additional scanning will be needed in order to be able if a full at least two dimensional image of the object is to be recorded, inducing a longer measurement time. Alternatively, if only a one dimensional differential image is to be obtained, a one dimensional pixelated detector may result directly in a full basic dataset. Examples of detectors 106 that may be used are photo-detectors, array detectors, flat panel detectors, CCD camera's, amorphous Si and CMOS flat panel detectors, TFT detector, etc. The detector 106 preferably is adapted for detecting an irradiation beam with wavelength as emitted by the irradiation source 102. The detector preferably has a high resolution and high contrast, as the latter may assist in ease for determining three dimensional location information about objects. In preferred embodiments, the amount of detector elements is large, e.g. such as in a 1024×1024 pixelated detector although other pixel configurations and another total number of pixels also can be used. The detector 106 may be positioned on a moveable stage in order to increase the field of view (not shown in FIG. 1). The detector 106 also may be positioned on a moveable stage in order to provide a different configuration between the detector 106 and the source 102 and/or object 104. The detector 106 furthermore may comprise a read-out circuitry 116 for the detected signal and may possibly also be cooled, using a cooling means 118. The at least one detector 106 furthermore may be a plurality of detectors 106, such as e.g. two detectors 106 as described above, whereby different detectors are used for the recording of two subsequent basic datasets, i.e. images, for different configurations between the irradiation beam of the irradiation source 102, the object 104 and the detector 106 used.

As described above, the imaging system 100 typically also may comprise a positioning means 110 for positioning the object 104 under study. The positioning means may comprise any of or a combination of a dilatation means 120 and a rotation means 122. In this way the object can be translated and or rotated resulting in a different configuration between detector 106, object 104 and irradiation beam of the irradiation source 102. The dilation means may be adjusted for providing a translation perpendicular to the axis source 102-detector 106, and/or for providing a translation in the direction along the axis source 102-detector 106. The dilatation means may be any suitable dilatation means allowing small movements, such as e.g. based on a piezo-moveable stage. The rotation means 122 typically may allow to relatively rotate the object 104 with respect to the irradiation source 102, or more particularly the incoming irradiation beam, and the detector 106. Such relative rotation also may be obtained by alternatively rotating the irradiation source 102 and/or the detector 106 with respect to the object 104, using another rotation means. Furthermore, relative movement of the irradiation source 102 and the detector 106 may be obtained by combining rotation of the sample to be studied and rotation of the irradiation source 102 and the detector 106. The positioning means may be positioned on air bearings in order to avoid shocks during positioning, shift, rotation and measurements.

The control means 108 for obtaining at least two different basic datasets, images, of the object 104 for different configurations may be adapted for providing a different configuration, i.e. positional configuration, of the irradiation source 102, the detector 106 and the object 104. The control means 108 therefore may be adapted for providing control signals to positioning means 110, e.g. dilatation means or rotation means, of the sample, positioning or irradiation beam altering means coupled to the irradiation source 102, positioning means of the detector 106, and/or driving means for different irradiation sources 102 and/or different detectors 106 if a plurality of them is used for acquiring the two basic datasets, i.e. images. The control means thus may provide appropriate configuration between the different components for the acquisition of the basic datasets, i.e. images. The controller 130 also may be adapted for synchronising the different components for appropriate acquisition of the different datasets, i.e. images. In this way the control means thus my control the acquisition of different basic datasets, i.e. images. The control means 108 may be operated by a user or it may be programmed as to operate in an automated and/or automatic way. The controller therefore may operate according to predetermined algorithms.

Using this control means 108 a different positional configuration between the at least one irradiation source 102, the at least one detector 106 and the object 104 to be characterised thus can be obtained. Such a different relative position may be obtained by moving the sample, moving the source, selecting a different source, moving the detector or selecting a different detector or a combination of any of these, as is controlled by the control means 108 as described above. The different relative position may for example be caused by a rotation of the sample, a translation of the sample in a direction non-parallel with the source-detector axis, e.g. perpendicular to the source-detector axis, a translation of the sample in a direction parallel with the source-detector axis, a translation of the source or the detector parallel or non-parallel with the original source-detector axis or any of these relative changes in position. A suitable shift that may be used may be more than 1 µm but sufficiently small in order to be able to correlate particular features detected in the first basic dataset, i.e. image, to features in the second basic dataset, i.e. image. Such a shift may e.g. be such that the corresponding image is shifted over at least one pixel, although also sub-pixel shifts may be performed such as for example shifts down to 0.1 times the pixelsize or down to 0.5 times the pixelsize. The shift may have an upper limit of a couple of mm, e.g. be smaller than 5 mm, preferably less than 3 mm, more preferably less than 1 mm. The shift may be smaller than 10% of the largest dimension of the field of view, or smaller than 5% of the largest dimension of the field of view or smaller than 3% of the largest dimension of the field of view. The rotation that may be used may be any suitable rotation. It may be for example a rotation over less than 3°, less than 2° or less than 1°, or—according to a particular embodiment—a rotation over 180° or a combination thereof. The system furthermore comprises an image processing means 112, e.g. image processor, adapted for generating a differential image from two basic datasets, i.e. images. The at least two basic datasets, i.e. images, e.g. two basic datasets, i.e. images, thereby are obtained by detecting a transmitted irradiation beam, transmitted through the object, for different relative positions between the irradiation source used, the object and/or the detector used, acquired using a control means 108 as described above. The image processing means 112 allows to remove the basic material of the object material, thus revealing internal features such as defects in the object and features of the external contours. The image processing means therefore may be adapted to process the basic datasets, i.e. images. Such processing may e.g. comprise or consist of any or a combination of dividing and/or subtracting both basic datasets resulting in a processed differential image. By a division and/or subtraction of the two basic datasets, i.e. images, one gets a new differential image of which the grey scale is not depending on the interaction of the basic material, but only on the local features of the object and their position with respect to external contour. Such a differential image thus may be a 2 dimensional image of the internal and external features of the object. Furthermore, taking into account the obtained information and the change of relative position of the different components, a 3 dimensional image can be obtained providing information about the three dimensional position of the internal features. The latter may e.g. be based on the difference in shift change of features in cases where a non-parallel beam is used. The direction and size of the shift of features inside the differential radiographs depend on the geometry of the beam, e.g. cone beam, and the amount of shift in positional configuration. A too large shift thereby is not recommended since the correlation of the shifted features becomes harder then. In preferred embodiments, the shape of the irradiation beam—influencing the magnification—and the amount of shift provided may be selected according to predetermined criteria.

Alternatively, e.g. if no non-parallel beam is used, additional information such as e.g. more differential images may be used by the image processing means 112 to provide 3D position information about the structural features visualised. The image processing means may be a processing means as will be described in more detail below.

It is an advantage of embodiments of the present invention that without the need for a large number of calculations, a direct 2D image of the internal and external features of the object can be obtained. The number of images required depends on the complexity of the object and the specific embodiment used. The method can be successfully used for a range of objects requiring only one differential image to determine the position of the features inside the object. More complex geometries require two, three or a small amount of 2D differential images, such as e.g. less than 3 differential images, or less than 5 differential images or less than 10 differential images, to fully locate the features in 3D. A classical CT scan typically requires hundreds of images to obtain 3D information. It is an advantage of embodiments of the present invention that the time required for obtaining a differential image, e.g. a 2 dimensional or 3 dimensional image of an object is short. It also is an advantage that the radiation dose required for obtaining a 2 dimensional or 3 dimensional image of an object is low, e.g. compared to conventional computed tomography applications the radiation dose required for imaging may be reduced with a factor 100. The present technique also may be combined with another imaging technique for obtaining confirmation, further or other information about the object, such as e.g. a computed tomography scan. The present technique also may be used as a first screening technique for obtaining characterisation information, whereby other, less time efficient, techniques can be performed on parts of interest of an object or on objects of interest.

Further components such as different cooling means, correction means for correcting shifts of the components due to stress or thermal influences, etc. also may be present in the characterisation system 100.

Figure 2:
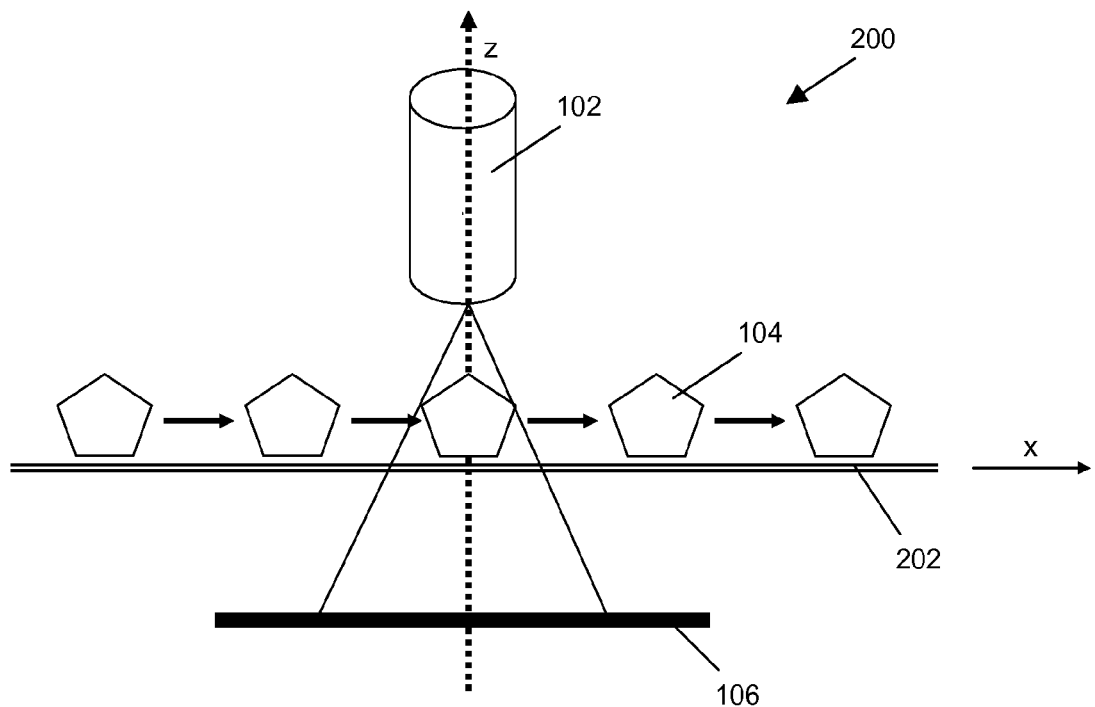
FIG. 2 is a schematic representation of part of a characterisation system according to a first particular embodiment of the first aspect of the present invention.

By way of example, the present invention not being limited thereto, the first aspect will be further illustrated using a number of particular embodiments. In a first particular embodiment according to the first aspect of the present invention, the characterisation system 200 comprises the positioning means 110 may be based on a translation means such as e.g. a conveyor belt 202 positioned substantially horizontally between the irradiation source 102 and the detector 106. An advantage of such a characterisation system 100 is that it may be used as a continuous flow through system. Such a system is shown by way of example in FIG. 2. The conveyor belt 202 in the present setup is transparent for the irradiation beam used. Alternatively, the irradiation source and the detector may be positioned such that no transmission of the irradiation through the conveyor belt is required. The movement of the conveyor belt then may be used as movement means for generating the different positional configuration. It is an advantage that no further additional positioning means are required, resulting in a less complex system. Alternatively or in addition thereto such a system also may rely on the use of different detectors and or different irradiation sources for obtaining the different positional configuration. When different detectors are used, the matrix of the object still will be removed by applying the differential imaging technique, but effects of detector responses will not be removed but on the contrary introduced for detector response effects of both detectors. It therefore may be advantageous to apply the technique using the same detector, so that no effects of detector response are present. The measurement times that are obtainable with such a system can be as low as 1 second per object, resulting in a fast characterisation system. A longer scanning time will increase the contrast and the signal to noise S/N ratio of the system.

In a second particular embodiment according to the first aspect of the present invention, the positioning means may be a pick-and-place system which positions the object on an object table. Depending on the position of the irradiation source 102 and the detector 106, the object table may be selected to be transparent for the irradiation beam. One example may be the use of a beryllium platform in combination with an X-ray irradiation beam.

Figure 3:
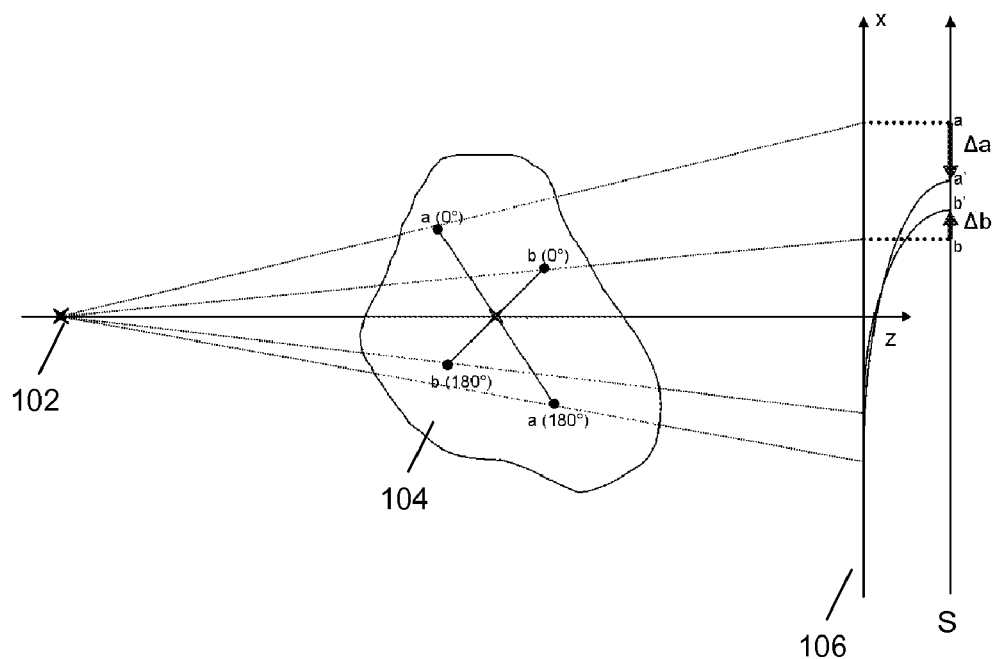
FIGS. 3 to 5 are schematic representations of part of a characterisation system according to respectively the third, fourth and fifth embodiment according to the present invention.
Figure 4:
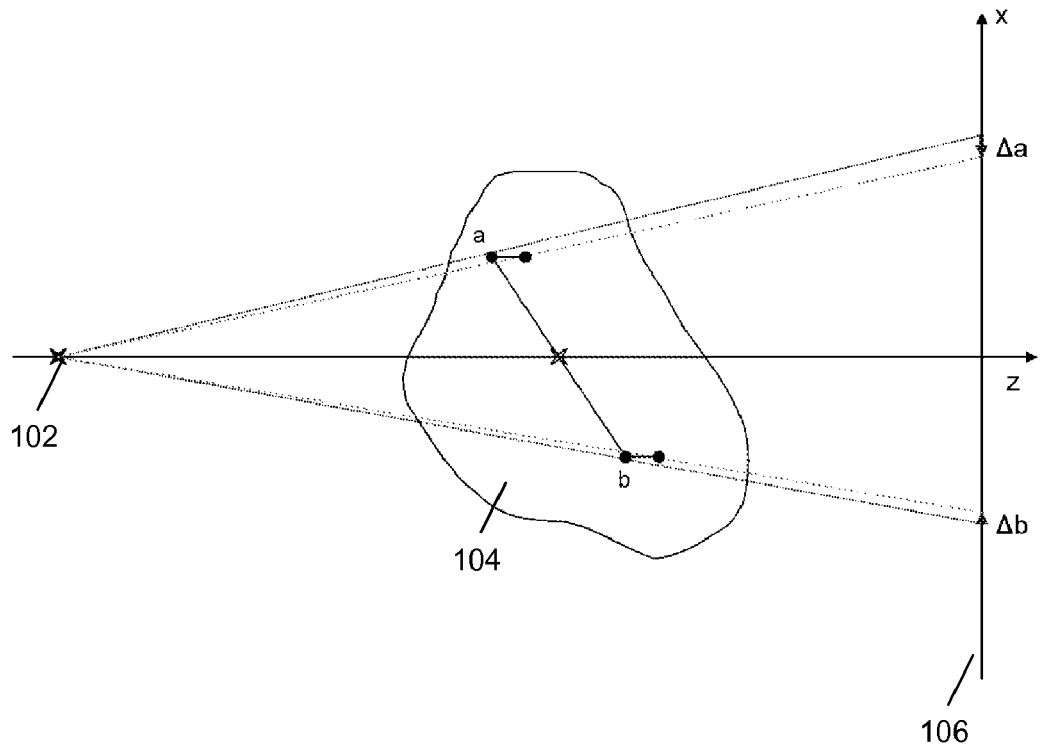

In a third particular embodiment, a characterisation system according to the first aspect is illustrated, whereby an irradiation source is provided generating a non parallel irradiation beam. The control means 108 is adapted for generating a second positional configuration whereby the object is rotated over 180° around an axis perpendicular to the line connecting the irradiation source with the detector and compared to a first positional configuration of object 104, detector 106 and irradiation source 102. The system thereby is adapted for removing the matrix of the object. In contrast to other embodiments, the method does not allow removing effects of the detector response efficiently. The image processing means 112 furthermore is adapted for processing the thus obtained basic datasets, i.e. images, by dividing and/or subtracting the first and second basic dataset, i.e. image, after one of the basic datasets, i.e. images, is mirrored. Using the resulting differential image allows to visualize the local defects. Furthermore, from the shift between the features in the different basic datasets, i.e. images, the location along the source 102-detector 106 axis can be determined. The positional configuration for recording both datasets, i.e. images, is illustrated in FIG. 3 showing an object with two features a and b and their positions in the two positional configurations, i.e.) a(0°) and b(0°) before rotation and a(180°) and b(180°) after rotation. The rotation axis R thereby crosses the axis irradiation source 102-detector 106 Z in a perpendicular way. The shifts Δa and Δb in position between the position of the imaged points a and b in the first basic dataset, i.e. image, and the position of the imaged points a' and b' in the mirrored second basic dataset, i.e. image, as seen in the image plane after processing S is also illustrated. In a fourth particular embodiment, a characterisation system according to the first aspect is illustrated, whereby an irradiation source is provided generating a non parallel irradiation beam. The control means 108 is adapted for generating a second positional configurations whereby the distance between the object 104 and the irradiation source 102 is changed in the direction of the irradiation source 102-detector 106 axis Z compared to a first positional configuration of object 104, detector 106 and irradiation source 102. In other words, a z-shift is used. The image processing means 112 furthermore is adapted for processing the thus obtained basic datasets, i.e. images, by any or a combination of dividing and/or subtracting the first and second basic dataset, i.e. image. Using the resulting differential image allows to visualize the local defects. Furthermore, from the difference in magnification between the features in the different basic datasets, i.e. images, the location of the features along the source 102-detector 106 axis Z can be determined, thus resulting in a 3D localisation of the features. The closer the feature is located to the source, the larger the shift that will occur. The positional configuration for recording both images is illustrated in FIG. 4 showing an object with two features a and b. The shifts Δa and Δb in position in the differential dataset, i.e. image, between the position of the imaged points a and b in the first positional configuration and in the second positional configuration, representative for the difference in magnification, is also indicated.

Figure 5:
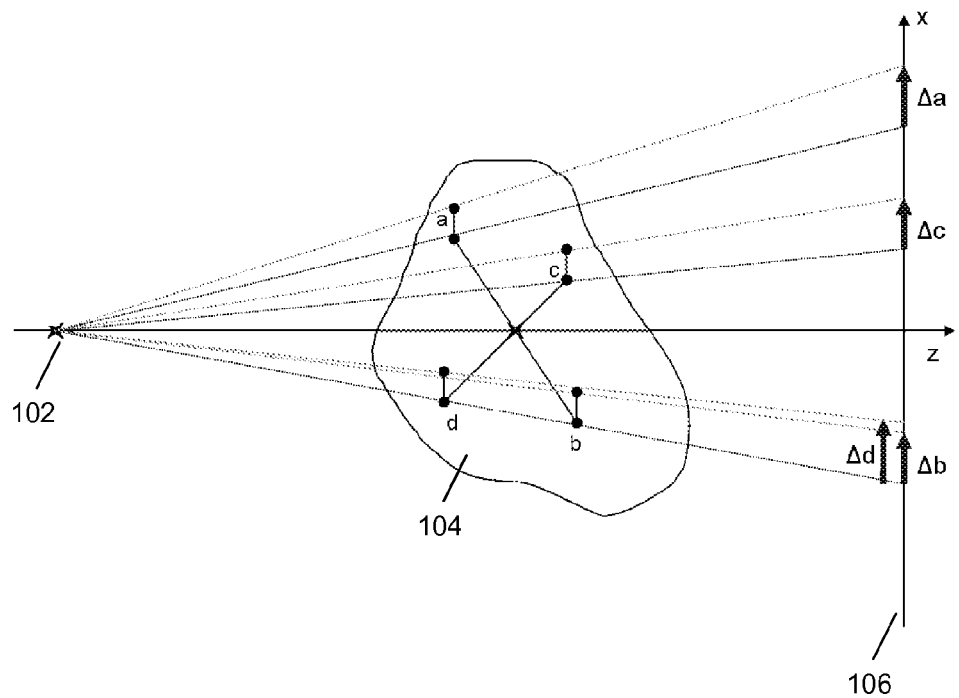

In a fifth particular embodiment, a characterisation system according to the fourth particular embodiment is shown, but whereby a shift in the direction perpendicular to the irradiation source 102-detector 106 axis Z is used. In other words, a shift in the x, y plane has occurred. As can be seen, four features a, b, c and d are present in the object and the shift in imaged points Δa, Δb, Δc and Δd are illustrated in FIG. 5. The positional information perpendicular to the irradiation source 102-detector 106 axis can be derived from the differential image, as well as their positional information along the irradiation source 102-detector 106 axis Z which can be derived from the magnitude of the shifts occurring. The closer the feature is located to the source, the larger the shift that will occur.

Figures 6A, 6B, 6C:
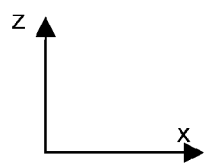
FIG. 6a to FIG. 6c is a schematic representation of shifts occurring in the basic datasets using a characterisation system as shown in FIGS. 3 to 5.

The third, fourth and fifth particular embodiment illustrate that with a geometry with non-parallel irradiation beam, e.g. a magnifying geometry whereby the irradiation source 102 is a point source, it is possible to determine the depth inside the object from a single differential radiography. The direction and size of the shift of features inside the differential radiographs depend on the geometry of the cone beam and the amount of shift. A too large shift thereby is not recommended since the correlation of the shifted features becomes harder then. In FIGS. 6a, 6b and 6c the magnitude of the shifts occurring for features in different areas of a hypothetical square object is illustrated with arrows for the third particular embodiment, the fourth particular embodiment and the fifth particular embodiment respectively. The positions discussed are with reference to the x-z plane for square objects positioned as indicated in FIG. 3, FIG. 4 and FIG. 5 respectively.

It is an advantage of embodiments according to the present invention that systems and methods can be obtained that they are especially suitable for material characterisation. More particularly it is an advantage of embodiments according to the present invention that systems and methods can be obtained for characterisation of diamonds. By selecting an X-ray irradiation source and an X-ray detector for characterisation of diamonds, the irradiation used suffers less from internal reflections inside the diamond, therefore resulting in an improved localisation of the feature in the diamond. The use of X-ray irradiation allows looking through the diamond without noticeable reflections in the projection image. One of the advantages of embodiments of the present invention is that it allows obtaining appropriate information about the features in the object, here the diamond, by cancelling out the bulk information of the diamond. Defects in diamonds can be identified inside a differential radiograph of the diamond, where all the different plains of the diamond are characterized by their own specific grey value. This is only possible by displacing the diamond into a well-known direction.

Figure 7:
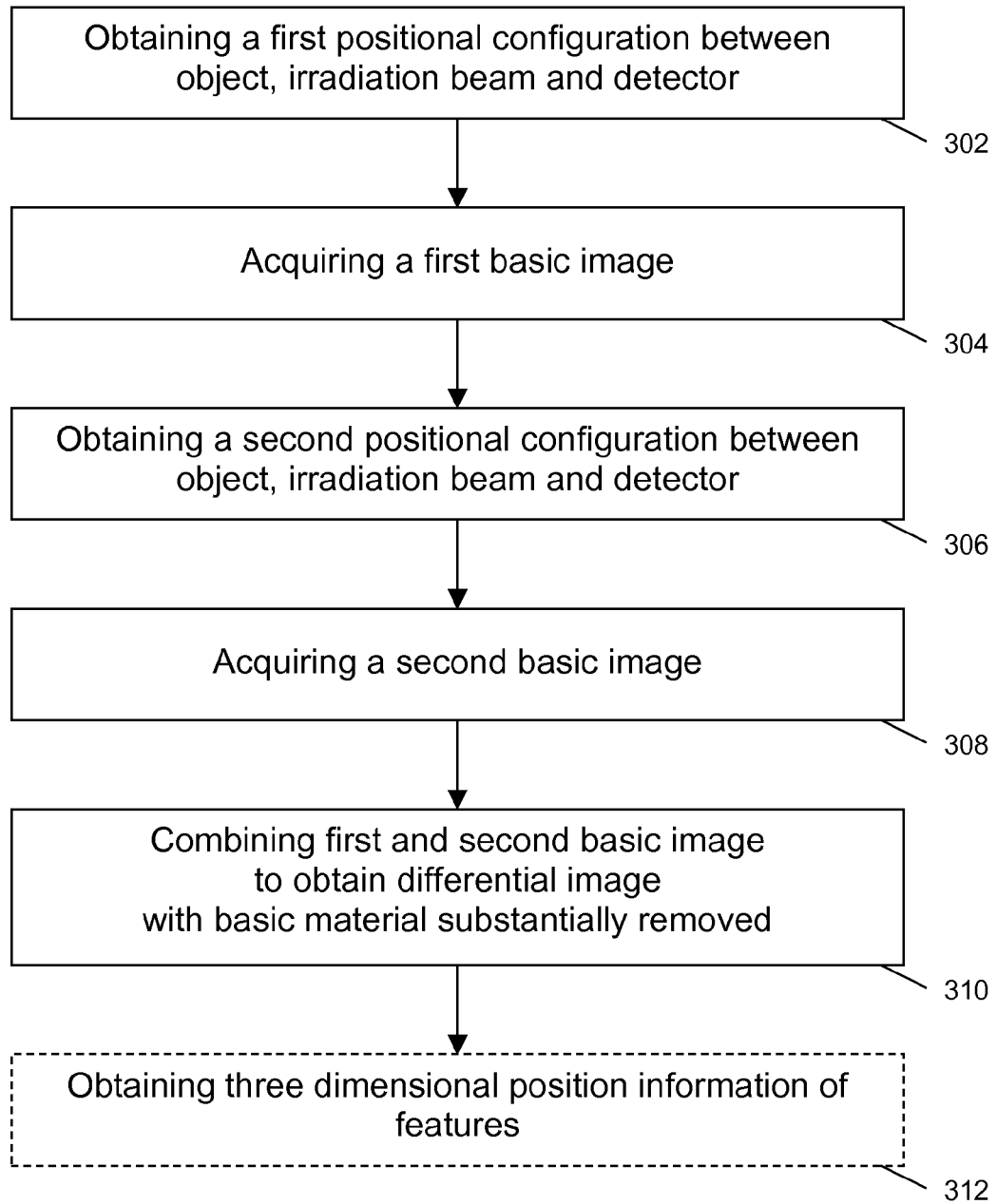
FIG. 7 is a schematic representation of an exemplary method according to embodiments of the second aspect of the present invention.

In a second aspect, the present invention relates to a method for characterising an object comprising a basic material and additional structural features. A schematic overview of an exemplary method according to the second aspect is illustrated in FIG. 7. The method may be performed using a characterisation system as described in embodiments of the first aspect, although the invention is not limited thereto. The method for characterising an object comprises obtaining at least two basic datasets, i.e. images, for different positional configurations for the irradiation beam, the object and the detector and combining the at least two basic datasets, i.e. images, for obtaining a differential image whereby the basic material substantially is removed. The method is described in more detail with reference to the exemplary method 300 of FIG. 7.

Prior to the step of providing a first configuration, calibration steps may be performed for calibrating the measurements for the characterisation system. Further steps that may be performed prior to performing the basic steps of the method may be for example preparing the sample.

A first step 302 comprises obtaining a first positional configuration between the object to be characterised, the irradiation beam used for irradiating the object and the detector used for acquiring the first basic dataset, i.e. image. Such a first positional configuration may be any standard configuration for which an image, e.g. radiographic image is taken. It may e.g. be providing an object in between an irradiation source and a detector. In one particular embodiment, obtaining a first positional configuration may comprise providing an object on a translating means such as e.g. a conveyor belt.

A second step 304 comprises acquiring a first basic dataset, i.e. image. Such a step preferably comprises irradiating the object with the irradiation beam and collecting the irradiation transmitted though the object using a detector. Irradiating thereby may be irradiating with an irradiation beam that is substantially penetrating for the object. Irradiating furthermore may comprise providing a flood irradiation for the object such that the full object or the full part of interest is irradiated at once. The step of acquiring may comprise synchronising the irradiation with the detection. Acquiring the first basic dataset, i.e. image, may be performed using a two dimensional detector. In particular embodiments, for example but not limited to embodiments using a conveyor belt, an image may be acquired by scanning the object using a one dimensional detector.

A third step 306 comprises obtaining a second positional configuration between the object, the irradiation beam and the detector. The second positional configuration thereby is different from the first positional configuration. Such a different configuration can be obtained by shifting the object with respect to the irradiation source 102-detector 106 axis. Such a shift may comprise a component along the irradiation source 102-detector 106 axis, a component perpendicular to the irradiation source 102-detector 106 axis a combination thereof. The different configuration also can be obtained by rotating the object, e.g. over 180° which will be followed by mirroring the image after acquisition and during processing. The latter method based on rotation allows removal of the matrix from the image, results in a better identification of defects in the object, but does not allow to remove effects of the detector response. The different configuration also can be obtained by shifting the irradiation source with respect to the object or the detector. The different configuration may e.g. be obtained by shifting the detector with respect to the object or the irradiation source. The different configuration also may be obtained by selecting a different irradiation source positioned at a different position than the irradiation source used for acquiring the first basic dataset, i.e. image, or by selecting a different detector positioned at a different position than the detector used for acquiring the first basic dataset, i.e. image. The different configuration furthermore also may be obtained by rotating the irradiation source and the detector with respect to the object. The different configuration also may be obtained by combining any of the above described shifts, rotations or selections. The shifts and rotations may be as set out in the first aspect. In one embodiment where the object is positioned on a conveyor belt, the different position may be obtained by translating the object on the conveyor belt. Obtaining a second positional configuration may be performed by controlling a translation or rotation means in the object table or a translation or rotation means of any of the irradiation source or detector.

In a fourth step 308, a second basic dataset, i.e. image, is acquired. Such an acquisition step may comprise the same features as acquisition step 304, but the positional configuration for which this is performed is the second positional configuration, being different from the first positional configuration by performing step 306.

In a fifth step 310, the first basic dataset, i.e. image, and the second basic dataset, i.e. image, are combined and processed to generate a differential image, e.g. a one dimensional differential image or e.g. an at least 2 dimensional differential image, indicating the additional features in the object and substantially filtering out the basic material. E.g. if a diamond is imaged, the resulting differential image will not show the standard bulk or raster material but will only indicate additional structural features of the object, such as inclusions, absorbing defects, edges, . . . . Combining the first basic dataset, i.e. image, and the second basic dataset, i.e. image, may be performed by subtracting or dividing the one basic dataset, i.e. image, by the other basic dataset, i.e. image. The resulting image, referred to as the differential image, indicates position information and shift of the features. As the background has been substantially removed from the differential image, the features are appropriately visualised, with a good contrast.

In a sixth, optional step 312, three dimensional localisation information may be obtained for the feature. For obtaining three dimensional localisation information, digital processing may be used.

Depending on the combining and processing of the data used in step 310, different types of initial digital processing may be performed. The initial digital processing may be digital processing to rescale the differential image to an average value of 0 for those image values corresponding to the signal of the matrix of the object. If for example division is used as combination and processing technique for the different datasets for generating the differential image, the image values representative for the matrix of the object will be on average 1 and the digital processing may comprise subtracting a value of 1 for all image values in the differential image. If for example subtraction is used as combination and processing technique for the different datasets for generating the differential image, the image values representative for the matrix of the object will be on average 0 and no subtraction of background is required. In this way an image is obtained wherein the matrix of the object is filtered out (has an average image value of 0) and wherein the processed image values for features inside the object differ from 0, thus becoming more easy to recognise, identify and segment. These features typically may contribute in the processed differential image data with both positive and negative components, i.e. corresponding with a first signal and a shifted signal with the opposite sign. In order to assist three dimensional localisation of the features, the one or more processed differential image data may be further digitally processed, allowing a better identification of the features. One way of further processing is by removing one of the positive or negative component by clipping the processed differential image data. Alternatively, a correlation technique may be applied to correlate each negative signal with a positive signal resulting in a less noise sensitive identification of features. Further segmentation of the one or more processed differential image datasets may be performed, for example by thresholding, resulting in setting a processed differential image value to 0 at positions where no large image signal contribution is present and thus no feature is to be expected and by setting the image value to 1 at positions where a significant image signal contribution is present and thus a feature is to be expected.

The actual three dimensional localisation of the features may be performed based on a single differential image or a plurality of differential images, as will be discussed for three different examples for 3D localisation of features. In one example, such information can be derived from the differential image if the acquisition is performed using a non-parallel irradiation beam and taking into account the shape of the irradiation beam and the amount of the shift that has occurred. The information thus may be based on a single differential image using a priori knowledge about the geometry of the acquisition setup for the differential image and the amount of shift or rotation that has occurred for obtaining the different datasets for acquiring the differential image. From the direction and the size of the features in the differential radiograph, the position along the irradiation source-detector axis can be detected, i.e. the depth in the object where the feature occurs. The combined information then results in a three dimensional localisation of the features. The latter may e.g. be represented in three dimensional image. In other words, due to the fact that the differential image is the result of capturing of data from two different orientations and optionally also due to the use of a diverging beam, e.g. a conical beam, additional information regarding the position of the features inside the object is embedded in the differential image.

Figure 8A:
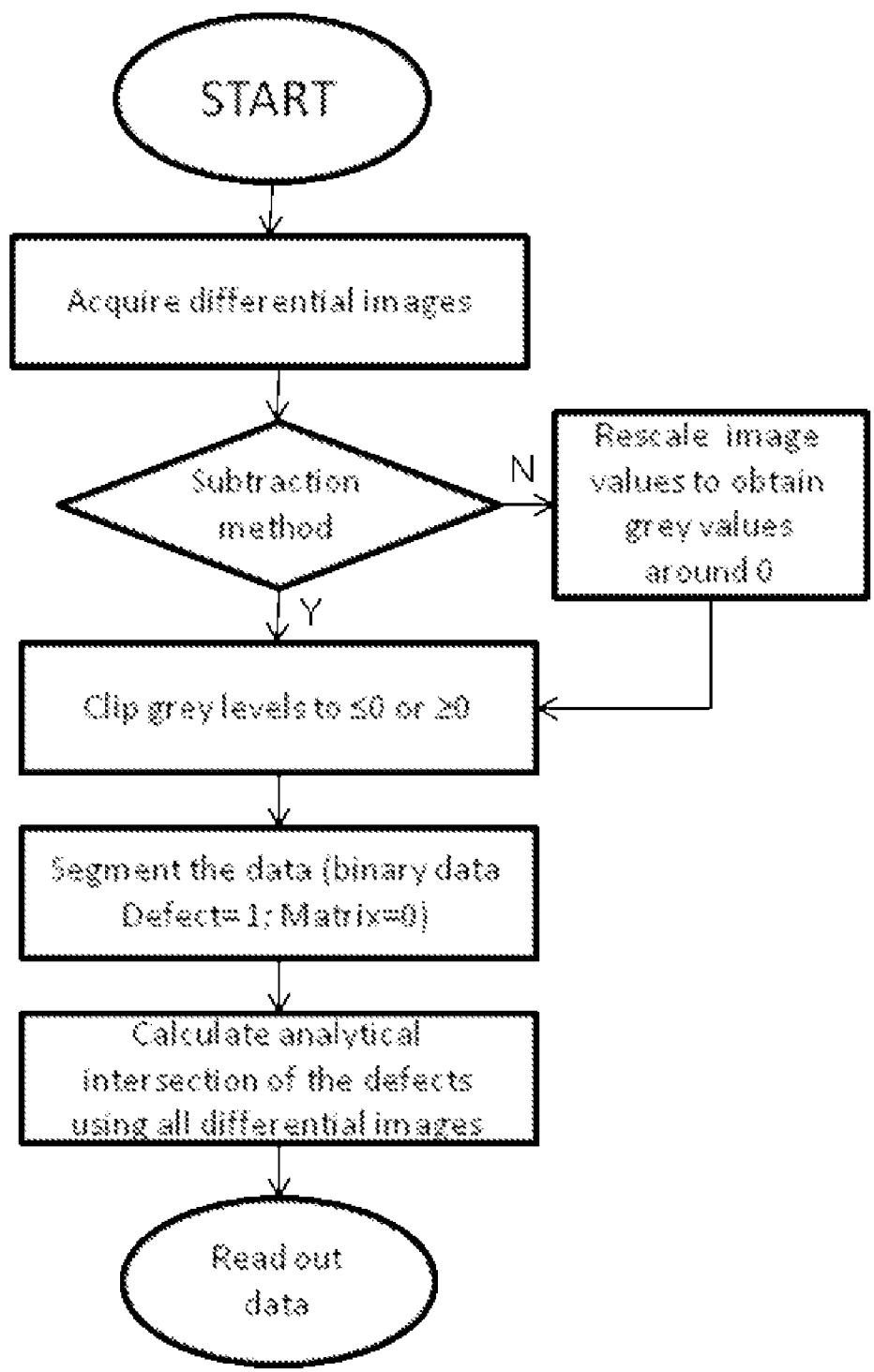
FIG. 8a and FIG. 8b illustrate optional steps for determining a three dimensional location of features as can be used according to embodiments of the present invention.

Alternatively or in addition thereto, obtaining position information also may be based using a plurality of differential images. In a first example thereof, localisation of features in an object may be based on analytical calculation of the position of features in the object. The latter may for example be performed based on segmented differential images acquired from substantially different directions with respect to the object. The shift or rotations used for acquiring differential images from different directions thereby are substantially larger, e.g. at least 5 times, such as for example at least one order of magnitude, than the shifts or rotations used for acquiring data for the production of a differential image as such. For this analytical calculation, the number of segmented differential images used may be more than 1 and less than 10. By way of illustration, the present invention not being limited thereto, a schematic representation of an exemplary method is shown in FIG. 8a. The method describes the acquisition of the differential images as set out above and further processing. After acquisition, an evaluation step is performed for evaluating whether a subtraction method is used for generating the differential image. If not the image first is resealed to set the matrix of the object to a value of substantially 0. Thereafter the grey levels are clipped as described above and segmentation of the data may be performed, i.e. a decision is made whether something belongs to a feature or not and thresholding is applied. The segmented images then are used for analytically calculating an intersection of the defects using the different differential images obtained. As a final step, the data may be read out.

Figure 8B:
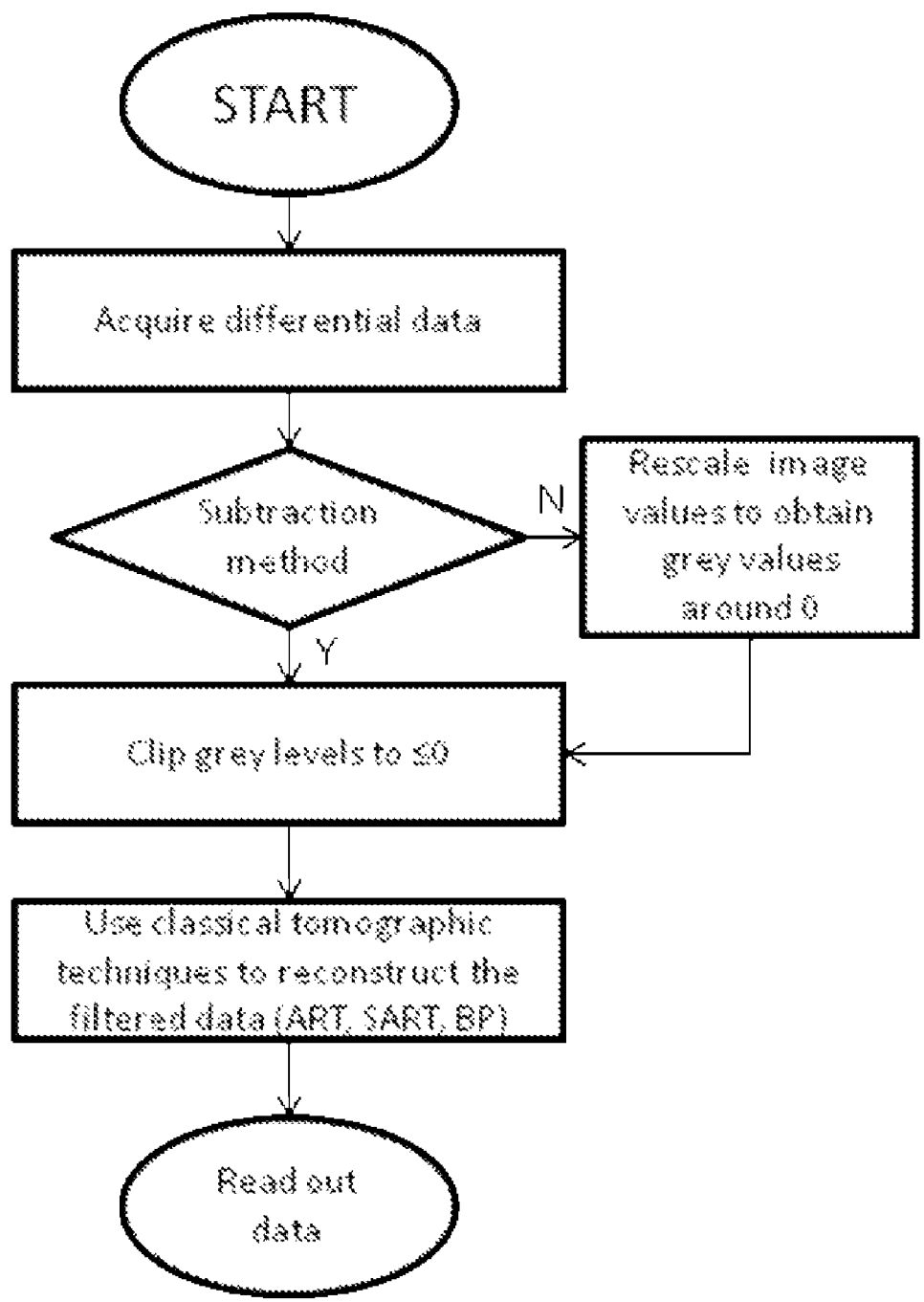

Another alternative or addition is the example of localisation of the features inside the objects based on using classical reconstruction techniques for the differential images. For example, the position may be determined using conventional reconstruction techniques such as back projection, Algebraic Reconstruction Techniques (ART), Simultaneous Algebraic Reconstruction Techniques (SART), . . . of the differential images. Classical reconstruction techniques with as input clipped and optionally also segmented differential images from the object usually require many differential images from the object, e.g. more than 50 differential images, such as for example more than 100 differential images. By way of illustration, the present invention not being limited thereto, a schematic representation of an algorithm is provided in FIG. 8b. The method is similar to the method as described in FIG. 8a, but segmentation is not performed. After clipping, in this case to positive values, the three dimensional location is determined using classical tomographic techniques for reconstruction.

By way of illustration, the present invention not being limited thereto, a further example is described, wherein the mathematical formulation comparing experimental generation of a differential image with generation of a differential image based on digital processing of a single dataset. Generation of a differential image with a fixed source, a fixed detector and a moving object results in a first basic dataset determined by $$I_1(x,y) = I_0(x,y) * \exp(-\mu(x,y)) * DR(x,y)$$

After a shift of $(\Delta x, \Delta y)$, a second basic dataset is given by $$I_2(x,y) = I_0(x,y) * \exp(-\mu(x-\Delta x, y-\Delta y)) * DR(x,y)$$

Upon division of both basic datasets, the resulting ratio is $$I_1/I_2 = \exp(-\mu(x,y) + \mu(x-\Delta x, y-\Delta y))$$

The latter illustrates that the obtained differential image is only dependent on the variation of the attenuation coefficient, whereby the attenuation coefficient $\mu$ is dependent on the local density and the material composition. It can be seen that effects of the detector or the configuration are not present in the resulting differential image.

By way of comparison, the differential image obtained by digital processing of a single dataset, i.e. by simulating a movement in the image, results in a first dataset determined by $$I_1(x,y) = I_0(x,y) * \exp(-\mu(x,y)) * DR(x,y)$$

And a second dataset determined by $$I_2(x,y) = I_1(x-\Delta x, y-\Delta y) = I_0(x-\Delta x, y-\Delta y) * \exp(-\mu(x-\Delta x, y-\Delta y)) * DR(x-\Delta x, y-\Delta y)$$

Upon division of both basic datasets, the resulting ratio becomes $$\begin{aligned}I_1/I_2 &= I_0(x,y) * \exp(-\mu(x,y)) * DR(x,y) / I_0(x-\Delta x, y-\Delta y) * \\ &\quad \exp(-\mu(x-\Delta x, y-\Delta y)) * DR(x-\Delta x, y-\Delta y) \\ &= I_0(x,y)/I_0(x-\Delta x, y-\Delta y) * \\ &\quad \exp(-\mu(x,y) + \mu(x-\Delta x, y-\Delta y)) * \\ &\quad DR(x,y)/DR(x-\Delta x, y-\Delta y)^*\end{aligned}$$

~ differential image * $\Delta$ detector response

The resulting image thus is a function of the experimentally obtained differential image and the detector response. The contributions of scattering and detector dark current can not be removed.

From the above formulas, it also can be seen that all effects influencing the attenuation coefficient $\mu$ will result in visualisation of the defect, such as for example scattering, diffraction, refraction, phase contrast or absorption. The method thus also can be used for generating phase contrast images.

It is an advantage of the method as described above that by processing, e.g. division or subtraction, of the two basic datasets, i.e. images, one gets a new differential image of which the grey scale is not depending on the interaction of the matrix, but only on the local features of the object and their position with respect to external contour. In this way, without additional calculations, a direct 2D image of the internal and external features of the object is obtained.

In a third aspect the present invention relates to a method and system for obtaining information about an object comprising basic material and additional structural features. The system comprises the same features and advantages as described in the first aspect, but has as an output the two basic datasets, i.e. images, which can externally be used for generating a differential image. In other words, the system is adapted for providing an output suitable for use in an image processing means, but does not comprise the image processing means itself. In similar way, the present invention also relates to the method for characterising an object but it only comprises acquisition of the basic datasets, i.e. images without comprising the image processing steps wherein the differential image is made. The method therefore comprises controlling the change in positional configuration as set out in the second aspect. The system therefore comprises the control means for controlling the selection of a second positional configuration as set out in the first aspect.

In a fourth aspect the present invention relates to a method for characterising an object, the object comprising basic material and additional structural features. The method comprises the fifth and optionally the sixth step as described for the method of characterising an object according to the second aspect.

Figure 9:
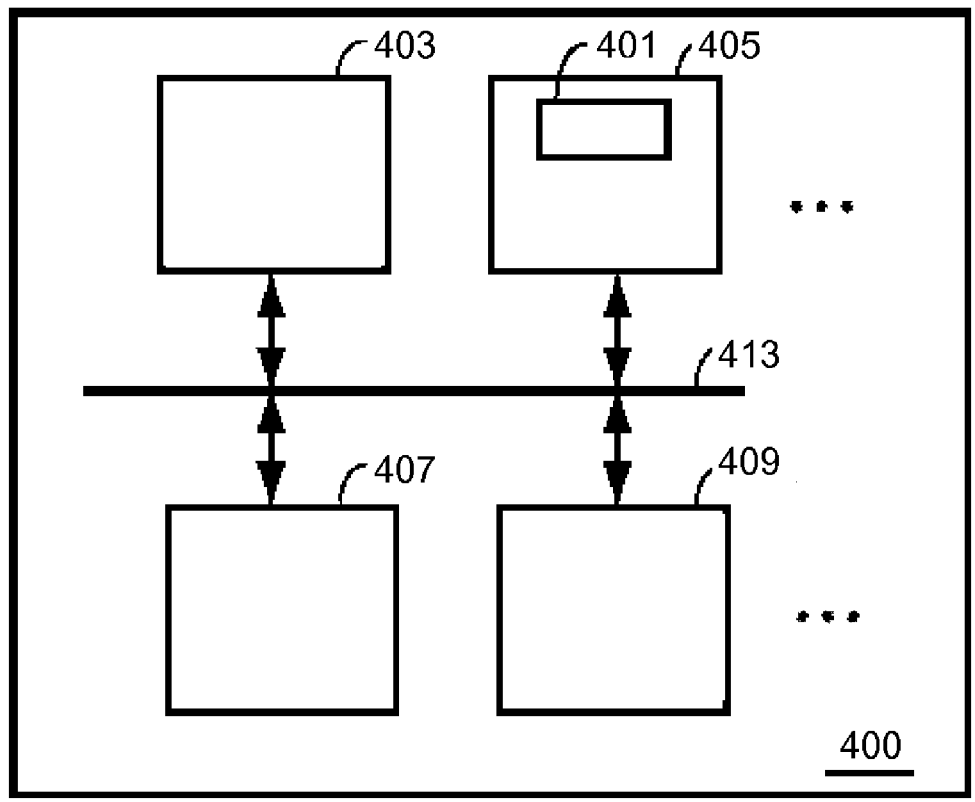
FIG. 9 is a schematic representation of an image processing means according to embodiments of an aspect of the present invention.

The above-described method embodiments related to characterising an object comprising basic material and additional structural features as described in the present invention may be implemented in a processing system 400, also referred to as computing means, such as shown in FIG. 9. FIG. 9 shows one configuration of processing system 400 that includes at least one programmable processor 403 coupled to a memory subsystem 405 that includes at least one form of memory, e.g., RAM, ROM, and so forth. It is to be noted that the processor 403 or processors may be a general purpose, or a special purpose processor, and may be for inclusion in a device, e.g., a chip that has other components that perform other functions. Thus, one or more aspects of the present invention can be implemented in digital electronic circuitry, or in computer hardware, firmware, software, or in combinations of them. The processing system 400, i.e. computing means 400, according to the present embodiment thus may be an image processing means for obtaining information about structural features in an object, the object comprising basic material and additional structural features. The image processing means thereby is adapted for receiving a first basic dataset, i.e. image, acquired for a first positional configuration and for receiving a second basic dataset, i.e. image, acquired for a second positional configuration, different from the first positional configuration. The image processing means furthermore is adapted for combining the first basic dataset, i.e. image, and the second basic dataset, i.e. image, into a differential image whereby the basic material is not present in the differential image. Combining the first basic dataset, i.e. image, and the second basic dataset, i.e. image, may comprise dividing one of the basic datasets, i.e. images, by the other. Combining the first basic dataset, i.e. image, and the second basic dataset, i.e. image, may comprise subtracting one of the basic datasets, i.e. images, from the other. In a particular embodiment, the image processing means furthermore is adapted for determining a three dimensional localisation of the features using information about the configuration used for acquiring the image and using the amount of shift or rotation applied between the first and second configuration used for acquiring the datasets, i.e. images. The image processing means thereby may be adapted for determining from the magnitude of the shift and the direction of the shift at what depth, i.e. what position along the irradiation source-detector axis, the imaged features are located. Ports for inputting and outputting data may be included in the image processing means. The processing system may include a storage subsystem 407 that has at least one disk drive and/or CD-ROM drive and/or DVD drive. In some implementations, a display system, a keyboard, and a pointing device may be included as part of a user interface subsystem 409 to provide for a user to manually input information. More elements such as network connections, interfaces to various devices, and so forth, may be included, but are not illustrated in FIG. 9. The various elements of the processing system 400 may be coupled in various ways, including via a bus subsystem 413 shown in FIG. 9 for simplicity as a single bus, but will be understood to those in the art to include a system of at least one bus. The memory of the memory subsystem 405 may at some time hold part or all (in either case shown as 411) of a set of instructions that when executed on the processing system 400 implement the steps of the method embodiments described herein. Thus, while a processing system 400 such as shown in FIG. 9 is prior art, a system that includes the instructions to implement aspects of the methods for characterising objects according to embodiments of the second or fourth aspect of the present invention is not prior art, and therefore FIG. 9 is not labelled as prior art.

The present invention also includes a computer program product which provides the functionality of any of the methods according to the present invention when executed on a computing device. Such computer program product can be tangibly embodied in a carrier medium carrying machine-readable code for execution by a programmable processor. The present invention thus relates to a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

By way of example, the present invention not being limited thereto, a number of examples are provided, illustrating features and advantages of the methods and systems described above.

In a first example, an object is characterised using a differential method as described above. The datasets, i.e. images, are obtained using a transmission type tube X-ray source with micro-focus or nano-focus and a high resolution X-ray CCD detector. Further imaging parameters are a source voltage of 60 kV, an exposure time of 4 s, a single frame record, a binning parameter of 1 and a pixel size of about 10 µm. In the present example, the differential image is obtained based on two radiographs taken at a different position perpendicular to the axis source-detector. Differential images thus obtained reveal the edges of the object. Furthermore, defects present in the object, if present, also are revealed. Where attenuation is too high, edges of the object may disappear in the noise. Using the same translation procedure, a higher contrast can be obtained in resulting images if the settings for the registration of the radiographs are adapted. One example resulting in higher contrast, but reduced resolution, is obtained by using a higher amount of frames, e.g. 10 frames, and using a higher binning parameter.

In a second example, visualisation of internal defects and edges of an object are obtained by obtaining a differential image from two shifted datasets, i.e. images. The datasets, i.e. images, are obtained with a transmission type X-ray tube having Fein-focus with a source voltage of 60 kV and using a Photonic Science VHR using an exposure time of 4 seconds and a binning parameter of 2. With increasing shift distance between the two basic datasets, i.e. images, improved contrast is obtained resulting in good visualisation of the internal defects and the edges of the object. Shifts between the datasets, i.e. images, may be for example over 50 nm, 150 nm, 300 nm, 600 nm, 1200 nm and 2400 nm 4800 nm, 9600 nm and 19200 nm. Smaller shifts may be less suitable for visualisations whereas larger shifts may be more suitable for visualisation of internal defects and the edges of the object. If the basic radiographic datasets, i.e. images, are recorded with a higher number of frames, the obtained images is improved. In the present example, a preferred result was obtained with a shift of 5 micrometer between the basic datasets, i.e. images, as this allowed best to reinforce the internal defects and to exclude the bulk of the object. The edges of the objects thereby are partially revealed at this shift distance, but the central part remains diffuse.

In a third example, visualisation of internal defects and the edges of an object is illustrated using differential radiography based on datasets, i.e. images, with a changed magnification. The example illustrates the possibility to enhance the contrast in the borders and the internal defects by excluding the internal defects and illustrates the possibility to identify the depth of the features in the object. In the present example, the different basic datasets, i.e. images, are obtained by changing the position of the object, parallel to the axis source-detector. The X-ray source used is a transmission type tube with a Fein-focus and the X-ray detector used is a Photonic Science VHR detector. Different results are obtained depending on the translation distance used. If the translation distance is low, the difference in magnification also is low and edges of the object are less well visualised. Preferred results are obtained for a shift of the object of 0.5 mm to 1 mm, whereby the distance source-detector is about 200 mm to 300 mm as a good contrast is obtained. The latter in the present example is obtained by changing the distance between source and object. The latter results in X-rays following slightly different paths, which make it possible to visualize defects and surfaces of the object. Providing selected magnification changes is preferred as for predetermined selected magnification changes preferred contrast of edges of the object can be obtained.

In a fourth example, visualisation of internal defects and edges of an object is obtained by obtaining a differential image from two basic datasets, i.e. images, obtained at an angle 0° and 180° of the object with respect to the incident light beam. The example again illustrates exclusion of the bulk information resulting in enhanced contrast to visualise the borders and the internal defects. The example illustrates the possibility of identifying the depth of features inside the object. The two basic datasets, i.e. images, used are the radiographs obtained at 0° and 180° rotation of the object around the CT-axis z. The radiograph of the object at 180° is mirrored and the resulting image is divided by the radiograph at 0 degrees. The datasets, i.e. images, are obtained using a transmission X-ray tube with Feinfocus and using a voltage of 80 kV and using an X-ray detector being a Photonic Science VHR detector. The obtained differential radiographic image based on the two basic datasets, i.e. images, allow to identify internal defects and edges of the object studied.

Figure 10:
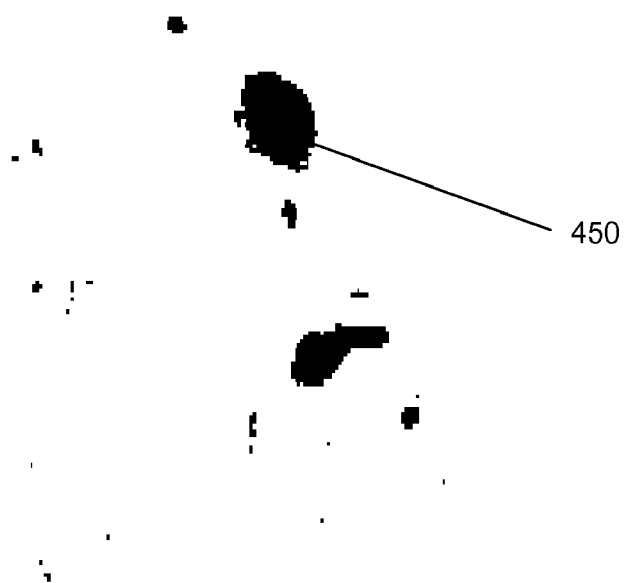
FIG. 10 illustrates a standard radiographic image of an object having multiple inclusions.
Figure 11:
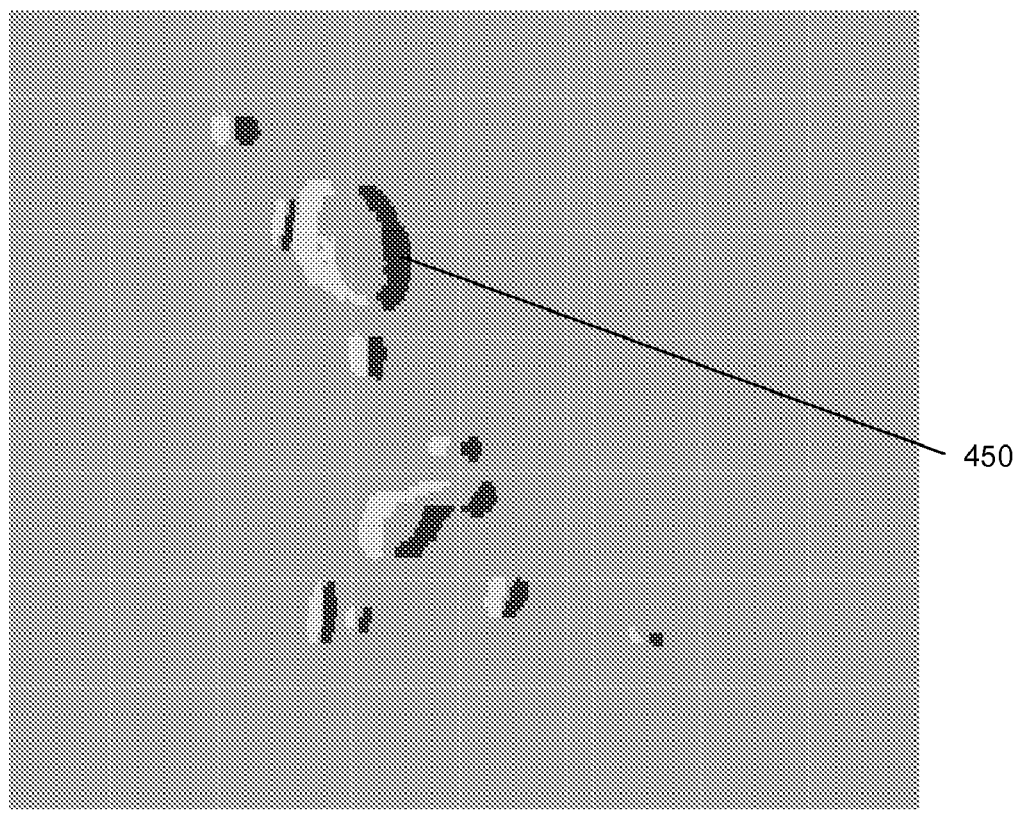
FIG. 11 and FIG. 12 illustrate a grey scale version and binary version of a differential X-ray image of the object as shown in FIG. 10, according to embodiment according to the present invention.
Figure 12:
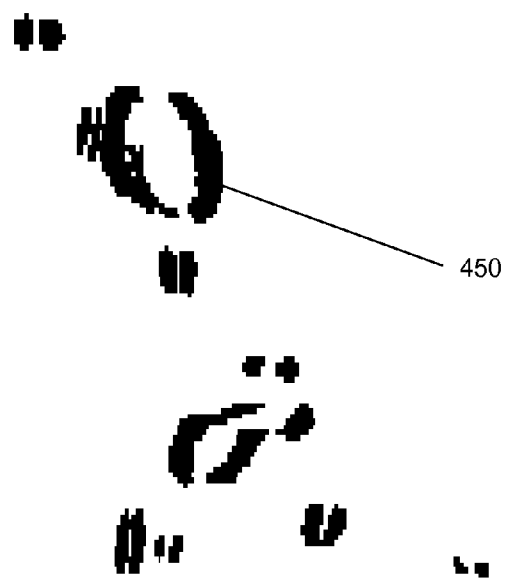

In a fifth example, images of an object 104 with a plurality of inclusions 450 are shown. FIG. 10 illustrates a standard X-ray image, whereas FIG. 11 and FIG. 12 are a gray scale respectively binary view of a differential image of the object. Comparison between FIG. 10 on the one hand and FIG. 11 and FIG. 12 on the other hands reveals that the differential imaging technique allows characterisation and detection of inclusions not visible with a standard X-ray image. The latter illustrates some of the advantages of embodiments according to the present invention.

By way of illustration, the present invention not being limited thereto, further examples and schematic illustrations of images that can be obtained using the present technique are discussed, and where appropriate, comparative examples are also provided.

Figures 13A, 13B, 13C:
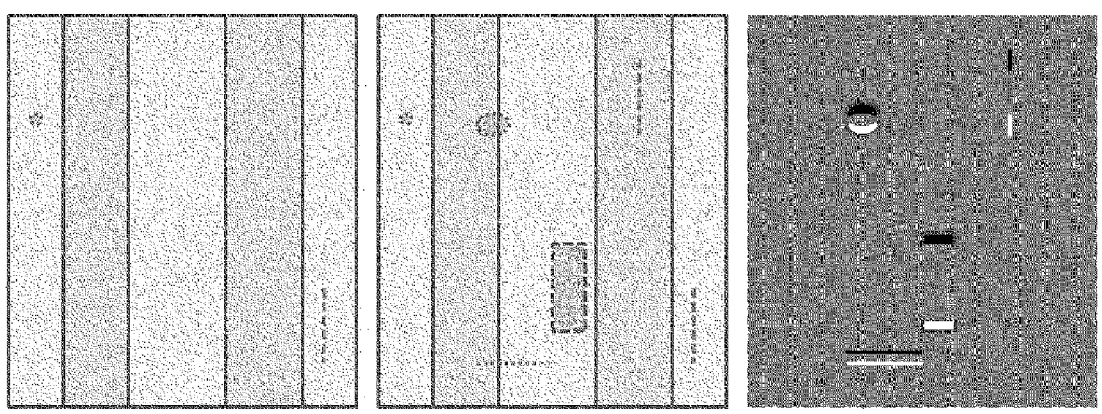

In a sixth example, a theoretical example of images that can be obtained using differential imaging is provided. FIG. 13a is a schematic illustration of an object without defect features, such as for example inclusions. The image shows the object with a plurality of detector defects, including bands, a defective detector column and a cluster of defective pixels. In FIG. 13b an image is shown of the same object, including inclusions. In practice it is difficult to distinguish detector defects from actual defects, such as inclusions, in the object. FIG. 13c illustrates a schematic representation of a differential image, wherein the detector defects are not visible anymore, whereas the defects in the object are clearly distinguishable over the contribution of the matrix of the object.

Figure 14A:
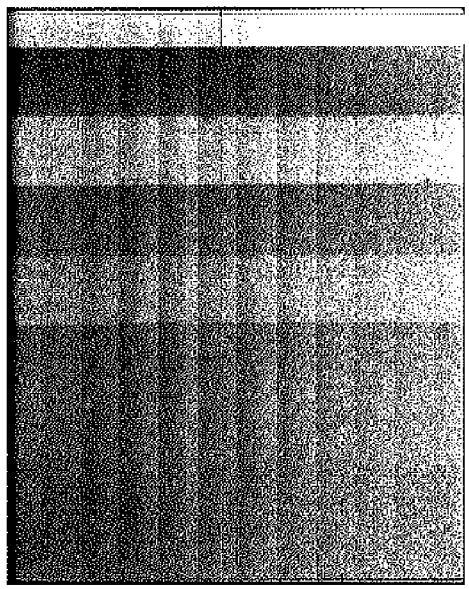
Figure 14B:
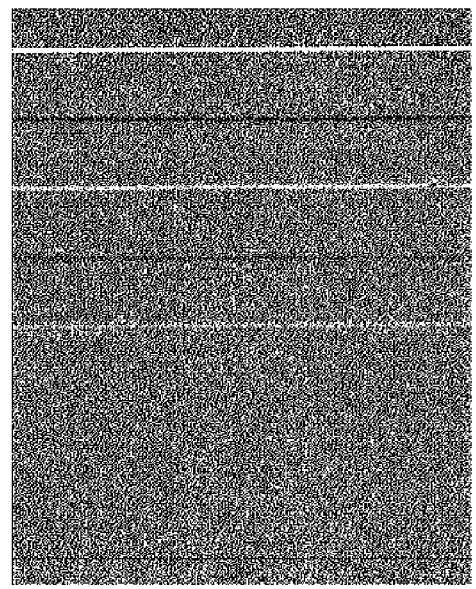

In a seventh example, an experimental example of a plastic plate with horizontal grooves is shown. The images are recorded with a Varian a-Si PaxSCAN 2520V detector, at a voltage of 80 kV and an energy of 2.7 W. In FIG. 14a an absorption image is shown, corrected for offset and flat field contributions, illustrating two grooves. As the grooves result in a smaller material thickness, less absorption is present and therefore a higher intensity is obtained. The vertical bands in the image are unwanted artefacts due to non-linearity of the detector response. In FIG. 14b, a differential image of the same object is shown. It can be seen that only the defects of the object can be seen and that the detector artefacts are not visible in the image.

Figure 15A:
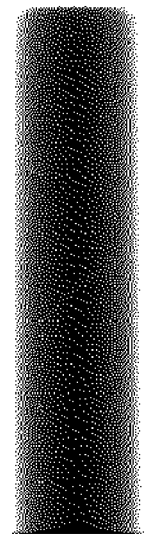

In an eighth example, a further experimental comparison of imaging of a plastic, cylindrically shaped object with defects is provided. In FIG. 15a, a classic X-ray absorption radiography image of the plastic cylinder is shown, wherein defects are hardly visible. In FIG. 15b and FIG. 15c differential images are shown of the same object. FIG. 15b thereby is a differential image obtained via digital processing of a single absorption image, by dividing the original single absorption image by a shifted version of the original single absorption image. FIG. 15c thereby is a differential image obtained by capturing two datasets and shifting the position in between the capturing of the two datasets over 20 pixels. It can be seen that the differential image has a better image quality as well as a better signal to noise ratio. The defects not visible in the X-ray absorption radiography image are visible in the differential image.

In a ninth example, an illustration is provided of an experimental detection of small and large defects in a plastic object. In FIG. 16a, an absorption image of the plastic plate is shown wherein the large defects are visible but wherein small defects such as holes and small scratches can be hardly recognised. In FIG. 16b, a differential image is shown wherein large defects as well as small defects are clearly imaged and can be easily segmented. Further, contrary to the absorption image, the differential image does not show effects of the detector response.

In a fifth aspect, the present invention relates to a characterisation system and method for characterising objects, more particularly for visualizing internal features and external features or contour features of an object, whereby the detection sensitivity and/or spatial resolution is high. The latter is obtained by exploiting the phenomenon of phase contrast. The fifth aspect of the present invention relates to any radiographic imaging technique for visualizing or characterising internal features and external features or contour features of an object. In preferred embodiments, the exploitation of phase contrast is applied in a system and method for performing differential X-ray as set out in any of the above described aspects of the present invention. Phase contrast can be explained based on the following principle. If the irradiation beam, e.g. X-ray beam, used for illuminating the sample penetrates the sample or object to be studied, the X-ray beam undergoes both absorption and phase shifts due to the differences of refractive index between within the sample. This leads to local deviations in the direction of propagation of the wave front, which causes intensity fluctuations when propagating beyond the sample. The latter results in an enhanced contrast around the outer borders of the sample and at structural differences inside the sample, which can be referred to as edge enhancement. More precisely local changes in the refractive index perpendicular to the direction of propagation lead to strong phase contrast effects.

According to the fifth aspect of the present invention, the characterisation system and method for characterising objects is adapted for visualizing internal features and external features or contour features of an object by promoting phase contrast. The systems and methods according to the present aspect therefore may be adapted for recording a phase contrast image, i.e. an image of the object comprising phase contrast features for the internal features and external features to be detected. The systems and methods may be adapted for extracting phase contrast information. It is to be noticed that for X-rays the refraction indices for most materials are close to 1, resulting in small angular deviations, typically of the order of 100 micrometer per meter of propagation distance. The system may be characterised by system parameters that are selected or tuned to make phase contrast observable on the recorded and processed differential images.

The irradiation source may be any suitable irradiation source as described in any of the above embodiments of the present invention. The selected system parameters may comprise a focal spot size of the source being sufficiently small, e.g. smaller than 100 µm, preferably smaller than 20 µm, more preferably smaller than 10 µm, even more preferably smaller than 5 µm. The detector may be any suitable detector as described in any of the above embodiments of the present invention. The selected system parameters may comprise a pixel size on the detector being sufficiently small, e.g. smaller than 100 µm, preferably smaller than 50 µm even more preferably smaller than 25 µm. The selected system parameters may comprise a propagation distance between the sample or object to be measured and the detector being sufficiently larger, e.g. more than 25 cm, preferably more than 30 cm. Other optional components may be as described in any of the above described embodiments for the present invention.

The effect of phase contrast enhancement is illustrated in FIG. 17 showing the system setup with the irradiation source 102, the object 104 to be characterised and the detector 106. In the present example, the object 104 is a thin rectangular plate with a small internal features. FIG. 17 furthermore illustrates the intensity profile 502 that would result for the imaged object without phase contrast, and the intensity profile 504 that would result for the imaged object with phase contrast. It can be seen that the small internal feature in the image with phase contrast is significantly more pronounced that in the image without phase contrast.

It is an advantage of embodiments according to the present invention, that by exploiting the phase contrast effect, the sensitivity for detecting features is enhanced. In this way, features may be revealed that remain undetected based on absorption contrast alone. It also is an advantage of embodiments according to the present invention that by exploiting the phase contrast effect, the range of possible measurement conditions is enlarged, resulting in the possibility to lower the measurement times and/or the radiation doses.

It is an advantage of embodiments of the present invention that three dimensional information can be obtained in a fast and simple way. It is an advantage of some embodiments of the present invention that the methods and systems especially provide the possibility to obtain information on objects having a uniform density and containing inclusions/cavities/defects with a different x-ray absorption coefficient than the basic material, i.e. the matrix.

It is to be understood that although preferred embodiments, specific constructions and configurations, as well as materials, have been discussed herein for devices according to the present invention, various changes or modifications in form and detail may be made without departing from the scope and spirit of this invention. Functionality may be added or deleted from the block diagrams and operations may be interchanged among functional blocks. Steps may be added or deleted to methods described within the scope of the present invention.

The invention claimed is:

1. A characterisation system for characterising an object including a basic material and additional structural features, the system comprising at least one irradiation source for generating an irradiation beam for irradiating the object to be characterised and at least one detector for detecting said irradiation beam transmitted through the object, the system furthermore comprising a control means adapted for controlling said characterization system to obtain at least two different basic datasets of the object for different positional configurations of the irradiation beam, the object and the detector; and an image processing means adapted for combining said at least two different basic datasets obtained for said different positional configurations and adapted for obtaining based thereon a differential image indicating the additional structural features of the object but substantially filtering out the basic material so that the basic material is not indicated in the differential image.

2. A characterisation system according to claim 1, wherein the differential image is an at least two-dimensional differential image.

3. A characterisation system according to claim 1, wherein the image processing means is adapted for any or a combination of dividing and/or subtracting the at least two different basic datasets.

4. A characterisation system according to claim 1, wherein the at least two different basic datasets consist of only two different basic datasets.

5. A characterisation system according to claim 1, wherein the at least one irradiation source is adapted for providing a flood irradiation of the object.

6. A characterisation system according to claim 1, wherein the basic material is substantially uniform and wherein the additional structural features are features of interest.

7. A characterisation system according to claim 1, wherein the control means is adapted for providing said different positional configurations of the irradiation beam, the object and the detector by providing a relative shift between any of the irradiation beam, the object and the detector.

8. A characterisation system according to claim 7, the detector having detector pixels of a predetermined size P, said relative shift resulting in a shift between the basic datasets of more than the predetermined pixel size P but less than 100% of the field of view of the imaging system.

9. A characterisation system according to claim 7, wherein the control means is adapted for providing at least a shift in the direction perpendicular to an irradiation source-detector axis.

10. A characterisation system according to claim 7, wherein the control means is adapted for providing at least a shift in the direction parallel to an irradiation source-detector axis.

11. A characterisation system according to claim 7, the characterisation system comprising at least two irradiation sources and/or at least two detectors, wherein the control means is adapted for providing said shift by selecting a different irradiation source and/or selecting a different detector for acquiring a second of the at least two basic datasets.

12. A characterisation system according to claim 1, wherein the control means is adapted for providing said different configurations of the irradiation beam, the object and the detector by providing a relative rotation between any of the irradiation beam, the object and the detector.

13. A characterisation system according to claim 12, wherein the control means is adapted for providing a relative rotation of less than 5°.

14. A characterisation system according to 1, wherein the irradiation source is adapted for generating a nonparallel irradiation beam, and the image processing means furthermore is adapted for deriving three-dimensional positional information based on said differential image.

15. A characterisation system according to claim 14, wherein the three-dimensional positional information is derived taking into account a shift of imaged internal features between the at least two different basic datasets.

16. A characterisation system according to claim 1, wherein the image processing means is adapted for deriving three dimensional positional information based on a combination of a plurality of differential images.

17. A characterisation system according to claim 1, the system being adapted for extracting phase contrast information of the additional features.

18. A method for characterising an object including a basic material and additional structural features, the method comprising
obtaining at least two different basic datasets of the object for different positional configurations of the object and at least one irradiation source and at least one detector used for imaging the object;
combining the at least two different basic datasets obtained for said different positional configurations and obtaining based thereon a differential image indicating the additional structural features of the object but substantially filtering out the basic material.

19. An image processing means for use in characterisation of objects comprising a basic material and additional structural features, the image processing means being adapted for
receiving a first basic dataset acquired for a first positional configuration and for receiving a second basic dataset acquired for a second positional configuration, different from the first positional configuration, and
combining the at least two different basic datasets obtained for said different positional configurations and obtaining based thereon a differential image indicating the additional structural features of the object but substantially filtering out the basic material.

20. A non-temporal computer program product adapted for, when executed on a computing device, performing a method for obtaining an image of one or more volumetric sections of an object including a basic material, the method comprising:
obtaining at least two different basic datasets of the object for different positional configurations of the object and the at least one irradiation source and the at least one detector used for imaging the object;
combining the at least two different basic datasets obtained for said different positional configurations and obtaining based thereon a differential image indicating additional structural features of the object but substantially filtering out the basic material of the object.

* * * * *